United States Patent [19]

Hopwood

[11] Patent Number: 5,110,348
[45] Date of Patent: May 5, 1992

[54] GLYCINE COMPOUNDS AND HERBICIDAL COMPOSITIONS THEREOF

[75] Inventor: William J. Hopwood, Sittingbourne, England

[73] Assignee: Shell Internationale Research Maatschappij B.V., Netherlands

[21] Appl. No.: 548,190

[22] Filed: Jul. 5, 1990

Related U.S. Application Data

[63] Continuation of Ser. No. 150,989, Feb. 1, 1988, abandoned.

[30] Foreign Application Priority Data

Feb. 27, 1987 [GB] United Kingdom ............... 8704671

[51] Int. Cl.$^5$ ................. A01N 37/18; C07C 255/50
[52] U.S. Cl. ........................ 71/100; 71/105; 558/254; 558/415
[58] Field of Search ............... 558/254, 415; 71/100, 71/105

[56] References Cited

U.S. PATENT DOCUMENTS

| | | | |
|---|---|---|---|
| 3,340,042 | 9/1967 | Schwartz et al. | 71/94 |
| 3,515,744 | 6/1970 | Steinbrunn et al. | 71/105 |
| 3,853,938 | 12/1974 | Haddock et al. | 71/100 |
| 3,976,468 | 8/1976 | Fischer | 71/105 |
| 4,061,791 | 12/1977 | Hall et al. | 560/21 X |

OTHER PUBLICATIONS

Chemical Abstracts, vol. 107, 1987, 40474s.
Chemical Abstracts, vol. 87, 1977, 152154n.
Chemical Abstracts, vol. 67, 1967, 90273b.
Monatshefte Der Chemie, vol. 118, No. 2, Feb. 1987, Schmitt et al.
Tighineanu et al., Tetrahedron, vol. 36, 1980, pp. 1385–1397.

*Primary Examiner*—Joseph P. Brust
*Assistant Examiner*—Jacqueline Haley

[57] ABSTRACT

Novel herbicidal compounds of the general formula $$X-N-CH_2-C-LZ \atop | \quad \quad \| \atop O=C-Y \quad \; O \qquad (I)$$

in which

X represents a phenyl group substituted in the 2-position and optionally substituted in one or more of the 3-, 4-, 5- and 6-positions, the 2-substituent being a cyano group, or a group of the general formula $CQNR^1R^2$ or $COQR^3$ where Q represents an oxygen or sulphur atom and each of $R^1$, $R^2$ and $R^3$ represents a hydrogen atom or an optionally substituted alkyl, cycloalkyl, alkenyl, alkynyl, phenyl or phenalkyl group, or $R^1$ and $R^2$ jointly represent a hydrocarbon chain;

Y represents an optionally substituted phenyl group;

L represents an oxygen or sulphur atom; and

Z represents a hydrogen atom or an optionally substituted alkyl, cycloalkyl, alkenyl, alkynyl, phenyl or phenalkyl group;

and salts of such compounds.

12 Claims, No Drawings

GLYCINE COMPOUNDS AND HERBICIDAL COMPOSITIONS THEREOF

This application is a continuation of application Ser. No. 07/150,989, filed Feb. 1, 1988, abandoned.

This invention relates to novel glycine compounds, to their preparation, to their use in combating undesired plant growth, to compositions containing the compounds, and to intermediates for use in their preparation.

According to the present invention there are provided compounds of the general formula

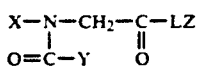

in which
- X represents a phenyl group substituted in the 2-position and optionally substituted in one or more of the 3-, 4-, 5- and 6- positions, the 2-substituent being a cyano group, or a group of the general formula or $CQNR^1R^2$ or $COQR^3$ where Q represents an oxygen or sulphur atom and each of $R^1$, $R^2$ and $R^3$ represents a hydrogen atom or an optionally substituted alkyl, cycloalkyl, alkenyl, alkynyl, phenyl or phenalkyl group, or $R^1$ and $R^2$ jointly represent a hydrocarbon chain;
- Y represents an optionally substituted phenyl group;
- L represents an oxygen or sulphur atom; and
- Z represents a hydrogen atom or an optionally substituted alkyl, cycloalkyl, alkenyl, alkynyl, phenyl or phenalkyl group;

and salts of such compounds.

Unless otherwise specified in this specification, an alkyl group may be linear or branched and suitably contains up to 10, preferably up to 6, and most preferably up to 4, carbon atoms, examples being methyl and ethyl. An alkenyl or alkynyl group preferably has up to 6 carbon atoms, especially up to 4 carbon atoms. A cycloalkyl group is preferably monocyclic and of 3 to 8 carbon atoms.

Unless otherwise stated in this specification, when any groups are designated as being optionally substituted, the substitutent groups which are optionally present may be any of those customarily employed in the development of pesticidal compounds, and/or the modification of such compounds to influence their structure/activity, persistence, penetration or other property. In relation to an alkyl group, including the alkyl moiety of a phenalkyl group, or an alkenyl, alkynyl, cycloalkyl or —$R^1$—$R^2$— hydrocarbon group, specific examples of such substituents include halogen, especially fluorine, chlorine or bromine atoms, and cyano, amino, mono- or di-($C_{1-4}$ alkyl)- amino and $C_{1-4}$ haloalkyl groups, and groups of the general formula $MR^4$ and $C(O)GR^4$ where M represents an oxygen or sulphur atom, G represents an oxygen or sulphur atom and $R^4$ represents a hydrogen atom, a $C_{1-8}$, especially $C_{1-4}$, alkyl group, a $C_{1-4}$ haloalkyl group or a phenyl group. It is generally preferred, however, that such alkyl, alkenyl, alkynyl, cycloalkyl or —$R^1$—$R^2$— hydrocarbon groups (for example, as $R^1$, $R^2$, $R^3$ and/or Z) in compounds of formula I are unsubstituted. In relation to a phenyl moiety, including the phenyl moiety of a phenalkyl group, optional substituents include halogen atoms, for example fluorine, chlorine, bromine and iodine atoms, and nitro, cyano, amino, mono- or di-($C_{1-4}$)alkylamino, $C_{1-4}$ alkyl, $C_{2-4}$ alkenyl, $C_{2-4}$ alkynyl and $C_{1-4}$ haloalkyl (especially $CF_3$) groups, and groups of formula $MR_4$, as defined above. A phenalkyl group is preferably phenyl-$C_{1-4}$alkyl-, most preferably benzyl.

In the definitions of the compounds of formula I given above, the 2-substituent of the group X is preferably a cyano group, or a group of the general formula $CONR^1R^2$ or $COQR^3$ where Q represents a sulphur or, preferably, an oxygen atom and each of $R^1$, $R^2$ and $R^3$ represents a hydrogen atom or an optionally substituted alkyl, phenyl or benzyl group. Most preferably each $R^1$, $R^2$ and $R^3$ represents an unsubstituted phenyl, benzyl or, especially, an alkyl group. Alternatively $R^1$ and $R^2$ may together represent an optionally substituted hydrocarbon group, preferably an alkylene group —$(CH_2)_m$— where m represents 2, 3 or 4. Most preferably, the substituent adjacent the linkage is a group of formula $CONH_2$ or $COO(C_{1-4}$ alkyl), for example ethoxycarbonyl, or, especially, a cyano group.

It is preferred that the group X is unsubstituted in the remaining positions, or substituted in 1 or 2 of these positions. If substituted, the group X is preferably substituted in the 3 or 6 position by a halogen atom. The further, optional, substituents of the group X may suitably be selected from the list given above but nitro groups and, especially halogen atoms, particularly fluorine and chlorine atoms, are preferred.

When the group X is substituted in positions additional to the 2-position, preferably at least one substituent is located in the 3-position.

Optional substituents of the phenyl group Y may be selected from the list given above. Preferred substituents are halogen atoms and nitro, $C_{1-4}$ alkoxy, (especially methoxy) $C_{1-4}$ haloalkyl (especially $CF_3$), $C_{1-4}$ alkyl, (especially methyl), $C_{1-4}$ alkylthio (especially methylthio), and phenoxy groups. Suitably the group Y is unsubstituted or substituted by 1, 2 or 3 moieties. When the group Y is substituted it is preferred that a substituent is located at the 4-position. Such a group Y is preferably unsubstituted at the remaining sites.

L preferably represents an oxygen atom.

Z preferably represents a hydrogen atom or an optionally substituted alkyl, phenyl or benzyl group. Most preferably, Z represents an unsubstituted benzyl, phenyl or, especially, alkyl group, conveniently ethyl.

Salts of compounds of formula I may be inorganic or organic salts, for example alkali metal or amine salts.

A preferred class of compounds of formula I may be defined as compounds of the general formula

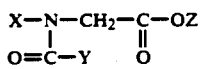

in which
- X represents a phenyl group substituted in the 2-position by a cyano group, or by a group of formula $CONR^1R^2$ or $COOR^3$ wherein each of $R^1$, $R^2$ and $R^3$ represents a hydrogen atom or an alkyl group, or $R^1$ and $R^2$ together represent an alkylene group, the phenyl group being optionally substituted in one or more of the 3-, 4-, 5- or 6- positions;
- Y represents an optionally substituted phenyl group; and
- Z represents a hydrogen atom or an optionally substituted alkyl, phenyl or benzyl group;

and salts of such compounds.

According to a further aspect of the present invention there is provided a process for the preparation of a compound of the formula I, wherein a compound of the general formula

X—NH—COY     (II)

is treated with an alkali metal hydride, especially sodium hydride, and the product is reacted with a compound of the general formula Hal—CH$_2$—COLZ     (III)

where Hal represents a halogen, especially bromine, atom.

Each of the steps described above is preferably carried in the presence of an organic solvent, suitably an aromatic hydrocarbon, for example xylene or toluene or, preferably, a cyclic ether, for example dioxan. Each of the reactions is preferably carried out at an elevated temperature, for example 40° C. to the reflux temperature, and conveniently at the reflux temperature. Isolation of the product of the first step is possible but is not necessary; preferably a 'one-pot' process for both steps is carried out.

A compound of the general formula II may be prepared by reacting an aniline of the general formula X—NH$_2$ with a benzoyl halide of the general formula Y—CO—Hal, where Hal represents a halogen, preferably chlorine atom; suitably in the presence of an organic base/solvent, for example pyridine or triethylamine, and optionally in the presence of a further organic solvent. The reaction is suitably effected under an inert atmosphere, for example nitrogen; and suitably at a temperature in the range 20° to 60° C., for example ambient temperature.

According to a further aspect of the invention there is provided a further process for the preparation of a compound of formula I, in which a compound of the general formula

X—NH—CH$_2$—COLZ     (IV)

is reacted with a benzoyl halide of the general formula Y—CO—Hal, where Hal represents a halogen, preferably chlorine, atom. Preferably, this method is carried out in an inert organic solvent, suitably a hydrocarbon, for example xylene, at an elevated temperature, for example 40° C. to the reflux temperature, preferably at the reflux temperature.

A compound of the general formula IV is suitably prepared by reacting an appropriate aniline X—NH$_2$ with a compound of the general formula III as defined above, preferably in the presence of an organic base/solvent, for example triethylamine, optionally in the presence of a further organic solvent; or in the presence of an organic solvent and an inorganic non-hydrolysing base, for example sodium bicarbonate. Examples of suitable organic solvents are alcohols, for example ethanol, or aromatic hydrocarbons, for example xylene. An elevated temperature, for example 40° C. to the reflux temperature, is preferably employed.

The group located at the 2-position of the phenyl group X in the compounds of formula I produced by the methods described above may be converted into one of the other groups, if desired, in standard manner. For example a cyano group at that position may be hydrolysed in standard manner to an amide, ester, acid or acid salt. Groups G, M and Z may also be derivatised in standard manner, if desired.

The alkali metal hydride derivatives of the intermediates of the general formula II are believed to be new. These intermediates therefore constitute a further aspect of the invention.

Some of the other intermediates of the general formula II are known, for example N-(2-cyanophenyl) benzamide (Chemical Abstracts Registry number 87223-76-5), 2-(benzoylamino)benzoic acid (Reg. No. 579-93-1) and its methyl and ethyl esters (Reg Nos. 751-49-8 and 42091-29-2). Believed to be novel, however, are compounds of the general formula II wherein X represents a phenyl group substituted in 2-position by a cyano group and optionally substituted in one or more of the 3-, 4-, 5- and 6-positions, and Y represents an optionally substituted phenyl group; provided that X is not 4-substituted; and provided also that when X is unsubstituted in the 3-, 4-, 5- and 6- positions Y does not represent a phenyl group optionally 2-substituted by a nitro or cyano group.

It is believed that the only intermediate of the general formula IV which is known is N-(2-cyanophenyl) glycine ethyl ester, (Heterocyclic Chemistry, 20, 495, 1983). A further aspect of the invention therefore provides intermediates of the general formula IV, but not N-(2-cyanophenyl)glycine ethyl ester.

Compounds of formula I have been found to show interesting activity as herbicides, showing high activity against undesirable grasses, such as barnyard grass, whilst low or no activity against useful, non-target species, including maize, rice, oat, linseed, mustard, sugar beet and soya. Accordingly, the invention further provides a herbicidal, especially graminicidal, composition comprising a compound of formula I as defined above in association with at least one carrier, and a method of making such a composition, which comprises bringing a compound of formula I into association with at least one carrier.

The invention also provides the use of such a compound or composition according to the invention as a herbicide, especially as a graminicide. Further, in accordance with the invention there is provided a method of combating undesired plant growth at a locus by treating the locus with a compound or composition according to the invention. The locus may for example be a crop area, for example a crop area containing plants or seeds of maize, oat, linseed, mustard, sugar beet, soya, wheat, barley, and rice (including paddy rice). Application to the locus may be pre-emergence or post-emergence. The dosage of active ingredient used may, for example, be from 0.01 to 10 kg/ha, preferably 0.05 to 4kg/ha. A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

The invention will now be further described with reference to the following Examples. The compounds were characterised by mass spectometry (M/e), CHN analysis and, when the compounds were solids, by melting point.

EXAMPLE 1

Preparation of
N-(4-chlorobenzoyl)-N-(2-cyano-3-fluorophenyl)-glycine, ethyl ester (a) 2-cyano-3-fluoroaniline (6.8g) was dissolved in pyridine (50ml) and stirred vigorously under dry nitrogen whilst 4-chlorobenzoylchloride (9.0g) was added in small portions over 10 minutes. The reaction mixture was stirred at ambient temperature overnight. Thin layer chromatography (tlc) showed that all the starting material had reacted. The reaction mixture was poured into ice/water and scratched until the gum which precipitated became solid. The solid, N-(4'-chlorobenzoyl)-2-cyano-3-fluorobenzanilide, was removed by filtration and crystallized from ethanol. Yield: 7.8g.

Analysis: Calculated %: 61.2C, 2.9H, 10.2N. Found %: 60.7C, 3.0H, 10.2N.

(b) The product of Example 1(a) (2.7g) was dissolved in dry dioxan (30ml) and stirred under nitrogen while 50% sodium hydride/paraffin oil (0.5g—i.e. 0.25g of NaH)) was added, in five portions. The reaction mixture was refluxed with stirring overnight and cooled to room temperature. To the reaction mixture, containing the desired intermediate N-(sodium)-N-(4'-chlorobenzoyl)-2-cyano-3-fluorobenzanilide, was added, in five portions, ethylbromoacetate (1.7g) in an equal volume of dioxan. After 30 minutes the reaction mixture was refluxed, and after 5 hours of reflux tlc analysis revealed that all the starting material had reacted. The dioxan was removed by evaporation and the residue treated with ethylacetate, washed with 2N hydrochloric acid, then water, then a saturated solution of sodium bicarbonate, then dried with anhydrous sodium sulphate, charcoaled, filtered and the filtrate evaporated, to yield the title compound (2.1g), mp 140.2° C., M/e 361 (Mw)=360.5).

Analysis: Calculated %: C, 59.9; H, 3.9; N, 7.8;. Found %: C, 59.6; H, 3.7; N, 7.8;.

EXAMPLE 2

Preparation of N-benzoyl-N-2-cyanophenylglycine, ethyl ester (a) 2-cyanoaniline (59g), ethyl bromoacetate (90g) and sodium bicarbonate (50g) were refluxed in ethanol (500ml), with stirring, for 42 hours. The reaction mixture was cooled slightly, filtered, and the filtrate cooled. The solid which formed was removed by filtration. Evaporation left an oil, containing unreacted starting material and the desired product, N-(2-cyanophenyl) glycine, ethyl ester. Trituration with ethanol and cooling gave the required product which after filtering was crystallized from ethanol.

Yield: 10.4g; mp: 92.3° C.

Analysis: Calculated %: C, 64.7; H, 5.9; N, 13.7. Found %: C, 64.3; H, 5.9; N, 18.8.

The preparation of this compound is also described in J. Heterocyclic Chem. 1983, 20, p. 495-8.

(b) The product of Example 2(a) (2.0g) and benzoyl chloride (1.6g) in xylene (50ml) were refluxed for 24 hours until gas evolution ceased. Solvent was removed by evaporation and the resulting gum was scratched under 40°-60° C. petroleum ether until solid. The solid was filtered off and crystallised from hexane, yielding the title compound as a white solid (2.7g), mp 88.1° C., M/e 309 (Mw=308).

Analysis: Calculated %: C, 70.1; H, 5.2; N, 9.1. Found %: C, 70.3; H, 5.3; N, 9.5.

Further compounds were prepared using procedures similar to those described above. Data on these compounds ar set out in Table 1 below.

TABLE 1

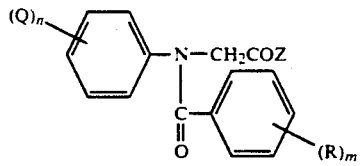

| Example | $(Q)_n$ | $(R)_m$ | Z | mp (°C.) | M/e/Mw | Analysis (CHN) Calculated % Found & | | |
|---|---|---|---|---|---|---|---|---|
| 3 | 2-CN | 4-Cl | $OC_2H_5$ | 111.5 | 343/342.5 | 70.1 | 5.2 | 9.1 |
|   |      |      |           |       |           | 70.4 | 5.2 | 9.2 |
| 4 | 2-CN | 2-F  | $OC_2H_5$ | 71.6  | 327/326   | 66.3 | 4.6 | 8.6 |
|   |      |      |           |       |           | 66.4 | 4.6 | 8.5 |
| 5 | 2-CN | 4-F  | $OC_2H_5$ | 93.1  | 327/326   | 66.3 | 4.6 | 8.6 |
|   |      |      |           |       |           | 65.8 | 4.4 | 8.2 |
| 6 | 2-CN | 4-$OCH_3$ | $OC_2H_5$ | gum | 339/338 | 67.5 | 5.3 | 8.3 |
|   |      |      |           |       |           | 67.8 | 5.3 | 7.9 |
| 7 | 2-CN | 4-$CF_3$ | $OC_2H_5$ | 70.3 | 377/376 | 60.6 | 4.0 | 7.4 |
|   |      |      |           |       |           | 60.6 | 3.8 | 7.2 |
| 8 | 2-CN | 4-Br | $OC_2H_5$ | 108.4 | 388/387 | 55.8 | 3.9 | 7.2 |
|   |      |      |           |       |           | 55.3 | 3.8 | 6.9 |
| 9 | 2-CN | 4-$CH_3$ | $OC_2H_5$ | 67.2 | 323/322 | 68.8 | 5.7 | 8.5 for hemihydrate |
|   |      |      |           |       |           | 68.8 | 5.4 | 8.8 |
| 10 | 2-CN | 4-I | $OC_2H_5$ | 100.1 | 435/434 | 48.7 | 3.6 | 6.3 for hemihydrate |
|   |      |      |           |       |           | 48.4 | 3.2 | 5.9 |
| 11 | 2-CN | 2,4-$Cl_2$ | $OC_2H_5$ | 135.4 | 378/377 | 55.9 | 3.9 | 7.2 for hemihydrate |
|   |      |      |           |       |           | 55.7 | 3.6 | 6.8 |
| 12 | 2-$CONH_2$ | 4-Cl | $OC_2H_5$ | 147.6 | 361/360.5 | 58.5 | 4.9 | 7.6 for hemihydrate |
|   |      |      |           |       |           | 58.3 | 4.5 | 7.3 |
| 13 | 2-$COOC_2H_5$ | 4-Cl | $OC_2H_5$ | 79.7 | 390/389.5 | 61.6 | 5.1 | 3.6 |
|   |      |      |           |       |           | 61.6 | 5.3 | 4.2 |
| 14 | 2-CN | 2-$OCH_3$ | $OC_2H_5$ | gum | 339/338 | 65.7 | 5.5 | 8.0 for hemihydrate |
|   |      |      |           |       |           | 66.0 | 5.2 | 7.5 |
| 15 | 2-CN | 3-F | $OC_2H_5$ | 87.3 | 327/326 | 66.3 | 4.6 | 8.6 |
|   |      |      |           |       |           | 65.9 | 4.6 | 8.6 |
| 16 | 2-CN, 4-$NO_2$ | 4-Cl | $OC_2H_5$ | 83.1 | 388/387.5 | 55.7 | 3.6 | 10.3 |
|   |      |      |           |       |           | 55.1 | 3.5 | 10.7 |
| 17 | 2-CN | 3-$OCH_3$ | $OC_2H_5$ | 91.7 | 379/378 | 67.5 | 5.3 | 8.3 |
|   |      |      |           |       |           | 67.3 | 5.3 | 8.4 |
| 18 | 2-CN, 4-Cl | 4-Cl | $OC_2H_5$ | 45.5 | 378/377 | 57.3 | 3.7 | 7.4 |
|   |      |      |           |       |           | 57.4 | 3.8 | 7.7 |
| 19 | 2-CN, 3-Cl | 4-Cl | $OC_2H_5$ | 84.2 | 378/377 | 55.9 | 3.9 | 7.3 for hemihydrate + |
| 20 | 2-CN | 4-Cl | $OCH_2Ph$ | gum | 405/404.5 | 68.2 | 4.2 | 6.9 |
|   |      |      |           |       |           | 68.2 | 4.6 | 7.0 |

TABLE 1-continued

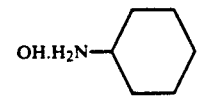

| Example | (Q)$_n$ | (R)$_m$ | Z | mp (°C.) | M/e/Mw | Analysis (CHN) Calculated % Found & |
|---|---|---|---|---|---|---|
| 21 | 2-CN | 3-Cl | OC$_2$H$_5$ | 40.7 | 343/342.5 | 63.1 4.4 8.2 / 62.5 4.4 8.4 |
| 22 | 2-CN | 4-NO$_2$ | OC$_2$H$_5$ | 125.4 | 354/353 | 61.2 4.2 11.9 / 60.9 4.1 11.8 |
| 23 | 2-CN, 3-F | 4-CF$_3$ | OC$_2$H$_5$ | 83.3 | 395/394 | 57.8 3.6 7.1 / 57.4 3.7 7.3 |
| 24 | 2-CN | 4-Cl | OH | 174.7 | 315/314.5 | 61.0 3.5 8.9 / 61.0 3.5 8.8 |
| 25 | 2-CN | 4-CF$_3$ | OCH$_2$-phenyl | gum | 439/438 | 65.7 3.9 6.4 / 65.8 3.9 6.5 |
| 26 | 2-CN | 4-CN | OC$_2$H$_5$ | 93.9 | 334/333 | 68.5 4.5 12.6 / 68.8 4.6 12.9 |
| 27 | 2-CN | 4-Cl | OCH$_3$ | 99.8 | 329/328.5 | 62.1 4.0 8.5 / 61.8 4.0 8.6 |
| 28 | 2-CN | 4-Cl | OH.HN(cyclohexyl)$_2$ | 201.8 | —/495 | 67.8 6.9 8.5 / 67.6 7.0 8.4 |
| 29 | 2-CN | 4-Cl | OCH$_2$.CH=CH$_2$ | 100.6 | 355/354.5 | 64.3 4.2 7.9 / 64.6 4.3 8.2 |
| 30 | 2-CN, 5-CF$_3$ | 4-Cl | OC$_2$H$_5$ | 142.2 | 411/410.5 | 55.5 3.4 6.8 / 55.7 3.5 7.0 |
| 31 | 2-CN | 4-Cl | O-t-butyl | 116.4 | 371/370.5 | 64.8 5.1 7.6 / 65.3 5.3 8.1 |
| 32 | 2-CN | 3-Cl, 4-Cl | OC$_2$H$_5$ | gum | 378/377 | 57.3 3.7 7.4 / 56.7 3.8 7.4 |
| 33 | 2-CN | 3-CF$_3$ | OC$_2$H$_5$ | 77.1 | 377/376 | 60.4 4.0 7.5 / 60.7 4.0 7.5 |
| 34 | 2-CN | 4-t-butyl | OC$_2$H$_5$ | 47.6 | 365/364 | 72.5 6.6 7.7 / 72.4 7.1 8.0 |
| 35 | 2-CN | 4-Cl | O-i-propyl | 85.3 | 357/356.5 | 63.9 4.8 7.9 / 63.7 4.7 7.9 |
| 36 | 2-CN | 4-Cl | O—CH$_2$—C≡CH | 140.7 | 353/352.5 | 64.7 3.7 7.9 / 64.4 3.7 7.9 |
| 37 | 2-CN, 6-F | 4-Cl | OCH$_2$C≡CH | 101.1 | 361/360.5 | 59.9 3.9 7.8 / 59.8 3.9 7.6 |
| 38 | 2-CN | 4-Cl | O(CH$_2$)$_2$O-n-butyl | gum | 415/414.5 | 63.7 5.5 6.8 / 63.7 5.2 6.8 |
| 39 | 2-CN | 4-Cl | SC$_2$H$_5$ | 153.8 | 359/358.5 | 60.3 4.2 7.8 / 60.2 4.2 7.8 |
| 40 | 2-CN | 4-SCH$_3$ | OC$_2$H$_5$ | 53.6 | 355/354 | 64.4 5.1 7.9 / 63.8 5.1 7.9 |
| 41 | 2-CN | 3-F, 5-F | OC$_2$H$_5$ | 73.6 | 345/344 | 62.8 4.1 8.1 / 62.9 4.2 8.2 |
| 42 | 2-CN | 3-F, 4-F | OC$_2$H$_5$ | 75.5 | 345/344 | 62.8 4.1 8.1 / 62.9 4.1 8.3 |
| 43 | 2-CN | 4-Cl | O(CH$_2$)$_7$CH$_3$ | gum | 427/426.5 | 67.5 6.3 6.6 / 67.2 6.4 6.4 |
| 44 | 2-CN | 3-O-phenyl | OC$_2$H$_5$ | gum | 401/400 | 72.0 5.0 7.0 / 72.1 5.2 7.1 |
| 45 | 2-CN, 3-F | 4-Cl | O-i-propyl | 79.2 | 375/374.5 | 60.9 4.3 7.4 / 60.8 4.2 7.5 |
| 46 | 2-CN, 3-F | 4-OC$_2$H$_5$ | OC$_2$H$_5$ | gum | 371/370 | 64.9 5.1 7.6 / 64.9 5.3 7.4 |
| 47 | 2-CN, 3-Cl | 4-OCH$_3$ | OC$_2$H$_5$ | gum | 373/372.5 | 61.2 4.6 7.5 / 61.0 4.7 7.4 |
| 48 | 2-CN | 4-O-i-propyl | OC$_2$H$_5$ | 94.7 | 367/366 | 68.8 6.0 7.7 / 68.9 6.0 7.8 |
| 49[1.] | 2-CN | 4-CH=CH$_2$ | OC$_2$H$_5$ | 78.9 | 335/334 | 69.9 5.5 8.2 / 69.9 5.5 8.3 |
| 50 | 2-CN | 4-Cl | OH.H$_2$N-cyclohexyl | 186.7 | —/413.5 | 63.8 5.8 10.2 / 63.8 5.8 10.1 |
| 51 | 2-CN | 4-Cl | O.CH$_2$CH$_2$F | 115.9 | 361/360.5 | 59.9 3.9 7.8 / 59.7 4.1 7.6 |

TABLE 1-continued

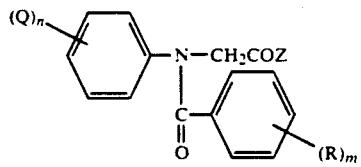

| Example | (Q)$_n$ | (R)$_m$ | Z | mp (°C.) | M/e/Mw | Analysis (CHN) Calculated % Found & | | |
|---|---|---|---|---|---|---|---|---|
| 52[1] | 2-CN | 4-Cl | [O-cyclohexyl] | 105.6 | 397/396.5 | 63.7 | 5.6 | 6.7 |
| | | | | | | 63.4 | 5.8 | 6.3 |
| 53 | 2-CN | 4-Cl | OCH$_2$CH$_2$—O—C$_2$H$_5$ | gum | 387/386.5 | 62.1 | 4.9 | 7.2 |
| | | | | | | 62.2 | 5.4 | 6.7 |
| 54 | 2-CN | 4-Cl | OC$_2$H$_5$ | 106.8 | 357/356.5 | 64.0 | 4.8 | 7.9 |
| | | | | | | 64.1 | 4.8 | 7.9 |
| 55 | 2-CN | 4-Cl | OH.HN(C$_2$H$_5$)$_2$ | 170.9 | —/387.5 | 61.9 | 5.7 | 10.8 |
| | | | | | | 61.7 | 5.7 | 10.6 |

+ This sample was dried and resubmitted for CHN analysis. The analysis for the dried sample was. calculated 57.3% C. 3.9% H. 7.4% N; found 57.4% C. 3.8% H. 7.4% N.
[1] Analysis figures given for hemihydrate.

HERBICIDAL ACTIVITY

Example 56

To evaluate their herbicidal activity, compounds according to the invention were tested using a representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 900 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0-9 scale. A rating 0 indicated growth as untreated control, whilst a rating 9 indicates death. An increase of 1 unit on the linear scale approximates to a 10% increase in the level of effect. The symbol * indicates that testing was not effected, for example because there was insufficient compound for all tests.

The results of the tests are set out in Table 2 below, in which the compounds are identified by reference to the preceding examples.

TABLE 2

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 2 | 0 | 0 | 8 | 0 | 0 | 0 | 0 | 0 | 5 | 0 | 0 | 8 | 2 | 2 | 3 | 0 | 2 | 0 | 0 | 7 | 0 | 0 | 0 | 0 | 0 |
| | | | | | | | | | 1 | 0 | 0 | 6 | 0 | 0 | 0 | 0 | 0 | 0 | 0 | 5 | 0 | 0 | 0 | 0 | 0 |
| 4 | 0 | 0 | 6 | 0 | 0 | 0 | 0 | 0 | 5 | 2 | 0 | 6 | 0 | 0 | 0 | 1 | 0 | 0 | 1. | 4 | 0 | 0 | 0 | 0 | 0 |
| | | | | | | | | | 1 | 0 | 0 | 3 | 0 | 0 | 0 | 0 | * | 0 | 0 | 1 | 0 | 0 | 0 | 0 | 0 |
| 15 | 0 | 0 | 9 | 0 | 0 | 0 | 0 | 0 | 5 | 1 | 0 | 8 | 0 | 0 | 0 | 0 | 0 | 0 | 0 | 7 | 0 | 0 | 0 | 0 | 0 |
| | | | | | | | | | 1 | 0 | 0 | 8 | 0 | 0 | 0 | 0 | 0 | 0 | 0 | 4 | 0 | 0 | 0 | 0 | 0 |
| 5 | 0 | 0 | 7 | 0 | 0 | 0 | 0 | 0 | 5 | 4 | 3 | 8 | 2 | 0 | 4 | 7 | 5 | 0 | 0 | 8 | 0 | 0 | 0 | 0 | 0 |
| | | | | | | | | | 1 | 0 | 0 | 7 | 0 | 0 | 0 | 1 | 1 | 0 | 0 | 7 | 0 | 0 | 0 | 0 | 0 |
| 3 | 0 | 0 | 8 | 0 | 0 | 0 | 0 | 0 | 5 | 0 | 0 | 8 | 0 | 3 | 0 | 0 | 0 | 0 | 0 | 8 | 0 | 0 | 0 | 0 | 0 |
| | | | | | | | | | 1 | 0 | 0 | 8 | 0 | 0 | 0 | 0 | 0 | 0 | 0 | 8 | 0 | 0 | 0 | 0 | 0 |
| 8 | 0 | 0 | 7 | 0 | 0 | 0 | 0 | 0 | 5 | 0 | 0 | 7 | 0 | 0 | 0 | 2 | 0 | 0 | 0 | 7 | 0 | 0 | 0 | 0 | 0 |
| | | | | | | | | | 1 | 0 | 0 | 7 | 0 | 0 | 0 | 0 | 0 | 0 | 0 | 7 | 0 | 0 | 0 | 0 | 0 |
| 10 | 0 | 0 | 6 | 0 | 0 | 0 | 0 | 0 | 5 | 0 | 0 | 5 | 0 | 0 | 0 | 0 | 0 | 0 | 0 | 7 | 0 | 0 | 0 | 0 | 0 |
| | | | | | | | | | 1 | 0 | 0 | 5 | 0 | 0 | 0 | 0 | 0 | 0 | 0 | 7 | 0 | 0 | 0 | 0 | 0 |

TABLE 2-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 6 | 0 | 0 | 6 | 0 | 0 | 0 | 0 | 0 | 5 | 0 | 0 | 8 | 0 | 0 | 0 | 4 | 2 | 0 | 0 | 7 | 0 | 0 | 0 | 0 | 0 |
| | | | | | | | | | 1 | 0 | 0 | 5 | 0 | 0 | 0 | 0 | 0 | 0 | 0 | 7 | 0 | 0 | 0 | 0 | 0 |
| 9 | 0 | 0 | 8 | 0 | 0 | 0 | 0 | 0 | 5 | 0 | 0 | 7 | 0 | 0 | 0 | 0 | 0 | 0 | 0 | 7 | 0 | 0 | 0 | 0 | 0 |
| | | | | | | | | | 1 | 0 | 0 | 6 | 0 | 0 | 0 | 0 | 0 | 0 | 0 | 7 | 0 | 0 | 0 | 0 | 0 |
| 7 | 0 | 0 | 6 | 0 | 0 | 0 | 0 | 0 | 5 | 0 | 0 | 6 | 0 | 0 | 0 | 0 | 0 | 0 | 0 | 7 | 0 | 0 | 0 | 0 | 0 |
| | | | | | | | | | 1 | 0 | 0 | 5 | 0 | 0 | 0 | 0 | 0 | 0 | 0 | 7 | 0 | 0 | 0 | 0 | 0 |
| 11 | 0 | 0 | 4 | 0 | 0 | 0 | 0 | 0 | 5 | 0 | 0 | 4 | 0 | 0 | 0 | 0 | 0 | 0 | 0 | 7 | 0 | 0 | 0 | 0 | 0 |
| | | | | | | | | | 1 | 0 | 0 | 2 | 0 | 0 | 0 | 0 | 0 | 0 | 0 | 5 | 0 | 0 | 0 | 0 | 0 |
| 13 | 0 | 0 | 5 | 0 | 0 | 0 | 0 | 0 | 5 | 3 | 0 | 7 | 0 | 1 | 0 | 3 | 1 | 0 | 0 | 7 | 0 | 0 | 0 | 0 | 0 |
| | | | | | | | | | 1 | 0 | 0 | 5 | 0 | 0 | 0 | 0 | 0 | 0 | 0 | 7 | 0 | 0 | 0 | 0 | 0 |
| 12 | 0 | 0 | 0 | 0 | 0 | 2 | 2 | 0 | 5 | 1 | 0 | 6 | 0 | 0 | 2 | 4 | 2 | 0 | 0 | 6 | 0 | 0 | 3 | 0 | 3 |
| | | | | | | | | | 1 | 0 | 0 | 4 | 0 | 0 | 1 | 2 | 0 | 0 | 0 | 2 | 0 | 0 | 3 | 0 | 0 |
| 1 | 0 | 0 | 9 | 0 | 0 | 0 | 0 | 0 | 5 | 4 | 0 | 8 | 2 | 3 | 2 | 0 | 2 | 0 | 0 | 8 | 0 | 0 | 0 | 0 | 0 |
| | | | | | | | | | 1 | 1 | 0 | 8 | 0 | 0 | 0 | 0 | 2 | 0 | 0 | 8 | 0 | 0 | 0 | 0 | 0 |
| 14 | 0 | 0 | 5 | 0 | 0 | 0 | 0 | 0 | 5 | 0 | 0 | 7 | 0 | 0 | 0 | 0 | 0 | 0 | 0 | 0 | 0 | 0 | 0 | 0 | 0 |
| | | | | | | | | | 1 | 0 | 0 | 3 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 5 | 0 | 0 | 6 | 0 | 0 | 0 | 0 | 0 | 0 | 0 | 0 | 0 | 0 | 0 | 0 | 0 |
| | | | | | | | | | 1 | 0 | 0 | 5 | 0 | 0 | 0 | 0 | 0 | 0 | 0 | 0 | 0 | 0 | 0 | 0 | 0 |
| 17 | 0 | 0 | 8 | 0 | 0 | 0 | 0 | 0 | 5 | 0 | 0 | 7 | 0 | 0 | 0 | 0 | 0 | 0 | 0 | 6 | 0 | 0 | 0 | 0 | 0 |
| | | | | | | | | | 1 | 0 | 0 | 6 | 0 | 0 | 0 | 0 | 0 | 0 | 0 | 2 | 0 | 0 | 0 | 0 | 0 |
| 18 | 0 | 0 | 7 | 0 | 0 | 0 | 0 | 0 | 5 | 0 | 0 | 6 | 0 | 0 | 0 | 0 | 0 | 0 | 0 | 7 | 0 | 0 | 0 | 0 | 0 |
| | | | | | | | | | 1 | 0 | 0 | 6 | 0 | 0 | 0 | 0 | 0 | 0 | 0 | 7 | 0 | 0 | 0 | 0 | 0 |
| 19 | 0 | 0 | 7 | 0 | 0 | 0 | 0 | 0 | 5 | 0 | 0 | 5 | 0 | 0 | 0 | 0 | 0 | 0 | 0 | 5 | 0 | 0 | 0 | 0 | 0 |
| | | | | | | | | | 1 | 0 | 0 | 4 | 0 | 0 | 0 | 0 | 0 | 0 | 0 | 3 | 0 | 0 | 0 | 0 | 0 |
| 20 | 0 | 0 | 6 | 0 | 0 | 0 | 0 | 0 | 5 | 0 | 0 | 7 | 0 | 0 | 0 | 0 | 0 | 0 | 0 | 7 | 0 | 0 | 0 | 0 | 0 |
| | | | | | | | | | 1 | 0 | 0 | 7 | 0 | 0 | 0 | 0 | 0 | 0 | 0 | 5 | 0 | 0 | 0 | 0 | 0 |
| 21 | 0 | 0 | 7 | 0 | 0 | 0 | 0 | 0 | 5 | 0 | 0 | 7 | 0 | 0 | 0 | 0 | 0 | 0 | 0 | 7 | 0 | 0 | 0 | 0 | 0 |
| | | | | | | | | | 1 | 0 | 0 | 6 | 0 | 0 | 0 | 0 | 0 | 0 | 0 | 5 | 0 | 0 | 0 | 0 | 0 |
| 22 | 0 | 0 | 6 | 0 | 0 | 0 | 0 | 0 | 5 | 0 | 0 | 8 | 0 | 0 | 0 | 0 | 0 | 0 | 0 | 0 | 0 | 0 | 0 | 0 | 0 |
| | | | | | | | | | 1 | 0 | 0 | 4 | 0 | 0 | 0 | 0 | 0 | 0 | 0 | 0 | 0 | 0 | 0 | 0 | 0 |
| 23 | 0 | 0 | 7 | 0 | 0 | 0 | 0 | 0 | 5 | 0 | 0 | 7 | 0 | 0 | 0 | 0 | 0 | 0 | 0 | 8 | 0 | 0 | 0 | 0 | 0 |
| | | | | | | | | | 1 | 0 | 0 | 7 | 0 | 0 | 0 | 0 | 0 | 0 | 0 | 8 | 0 | 0 | 0 | 0 | 0 |
| 24 | 0 | 0 | 8 | 0 | 0 | 0 | 1 | 0 | 5 | 0 | 0 | 8 | 0 | 1 | 0 | 0 | 0 | 0 | 1 | 8 | 0 | 0 | 0 | 0 | 0 |
| | | | | | | | | | 1 | 0 | 0 | 8 | 0 | 0 | 0 | 0 | 0 | 0 | 0 | 7 | 0 | 0 | 0 | 0 | 0 |
| 25 | 0 | 0 | 7 | 0 | 0 | 0 | 0 | 0 | 5 | 0 | 0 | 8 | 0 | 0 | 0 | 0 | 0 | 0 | 0 | 7 | 2 | 0 | 0 | 0 | 0 |
| | | | | | | | | | 1 | 0 | 0 | 5 | 0 | 0 | 0 | 0 | 0 | 0 | 0 | 5 | 0 | 0 | 0 | 0 | 0 |
| 26 | 0 | 0 | 6 | 0 | 0 | 0 | 0 | 0 | 5 | 0 | 0 | 5 | 0 | 0 | 0 | 0 | 2 | 0 | 0 | 4 | 0 | 0 | 0 | 0 | 0 |
| | | | | | | | | | 1 | 0 | 0 | 2 | 0 | 0 | 0 | 0 | 0 | 0 | 0 | 3 | 0 | 0 | 0 | 0 | 0 |
| 27 | 0 | 0 | 7 | 0 | 0 | 0 | 0 | 0 | 5 | 0 | 0 | 7 | 0 | 0 | 0 | 0 | 0 | 0 | 0 | 8 | 0 | 0 | 0 | 0 | 0 |
| | | | | | | | | | 1 | 0 | 0 | 7 | 0 | 0 | 0 | 0 | 0 | 0 | 0 | 8 | 0 | 0 | 0 | 0 | 0 |
| 28 | 0 | 0 | 8 | 0 | 0 | 0 | 1 | 0 | 5 | 0 | 0 | 8 | 0 | 1 | 0 | 0 | 0 | 0 | 0 | 7 | 0 | 0 | 0 | 0 | 0 |
| | | | | | | | | | 1 | 0 | 0 | 8 | 0 | 0 | 0 | 0 | 0 | 0 | 0 | 7 | 0 | 0 | 0 | 0 | 0 |
| 29 | 0 | 0 | 7 | 0 | 0 | 0 | 0 | 0 | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 7 | 0 | 0 | 0 | 0 | 0 | 0 | 0 | 6 | 0 | 0 | 0 | 0 | 0 |
| 30 | 0 | 0 | 0 | 0 | 0 | 0 | 0 | 0 | 5 | 0 | 0 | 3 | 0 | 0 | 0 | 0 | 0 | 0 | 0 | 0 | 0 | 0 | 0 | 0 | 0 |
| | | | | | | | | | 1 | 0 | 0 | 1 | 0 | 0 | 0 | 0 | 0 | 0 | 0 | 0 | 0 | 0 | 0 | 0 | 0 |
| 31 | 0 | 0 | 3 | 0 | 0 | 0 | 0 | 0 | 5 | 0 | 0 | 2 | 0 | 0 | 0 | 0 | 0 | 0 | 5 | 0 | 0 | 0 | 0 | 0 | 0 |
| | | | | | | | | | 1 | 0 | 0 | 2 | 0 | 0 | 0 | 0 | 0 | 0 | 3 | 0 | 0 | 0 | 0 | 0 | 0 |
| 32 | 0 | 0 | 7 | 0 | 0 | 0 | 0 | 0 | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 7 | 0 | 0 | 0 | 0 | 0 | 0 | 0 | 6 | 0 | 0 | 0 | 0 | 0 |
| 33 | 0 | 0 | 7 | 0 | 0 | 0 | 0 | 0 | 5 | 0 | 0 | 7 | 0 | 0 | 0 | 0 | 0 | 0 | 0 | 8 | 0 | 0 | 0 | 0 | 0 |
| | | | | | | | | | 1 | 0 | 0 | 6 | 0 | 0 | 0 | 0 | 0 | 0 | 0 | 6 | 0 | 0 | 0 | 0 | 0 |
| 34 | 0 | 0 | 5 | 0 | 0 | 0 | 0 | 0 | 5 | 0 | 0 | 7 | 0 | 0 | 0 | 0 | 0 | 0 | 0 | 7 | 0 | 0 | 0 | 0 | 0 |
| | | | | | | | | | 1 | 0 | 0 | 6 | 0 | 0 | 0 | 0 | 0 | 0 | 0 | 4 | 0 | 0 | 0 | 0 | 0 |
| 35 | 0 | 0 | 8 | 1 | 0 | 0 | 0 | 0 | 5 | 0 | 0 | 8 | 3 | 0 | 5 | 0 | 0 | 0 | 0 | 8 | 0 | 0 | 0 | 0 | 0 |
| | | | | | | | | | 1 | 0 | 0 | 7 | 1 | 0 | 3 | 0 | 0 | 0 | 0 | 7 | 0 | 0 | 0 | 0 | 0 |
| 36 | 0 | 0 | 8 | 0 | 0 | 0 | 0 | 0 | 5 | 0 | 0 | 8 | 1 | 0 | 0 | 0 | 0 | 0 | 0 | 8 | 0 | 0 | 0 | 0 | 0 |
| | | | | | | | | | 1 | 0 | 0 | 7 | 1 | 0 | 0 | 0 | 0 | 0 | 0 | 7 | 0 | 0 | 0 | 0 | 0 |
| 37 | 0 | 0 | 8 | 0 | 0 | 0 | 0 | 0 | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 7 | 0 | 0 | 0 | 0 | 0 | 0 | 0 | 7 | 0 | 0 | 0 | 0 | 0 |
| 38 | 0 | 0 | 8 | 0 | 0 | 0 | 0 | 0 | 5 | 0 | 0 | 9 | 0 | 0 | 0 | 2 | 1 | 0 | 0 | 8 | 0 | 0 | 0 | 0 | 0 |
| | | | | | | | | | 1 | 0 | 0 | 9 | 0 | 0 | 0 | 0 | 0 | 0 | 0 | 7 | 0 | 0 | 0 | 0 | 0 |
| 39 | 0 | 0 | 8 | 0 | 0 | 0 | 0 | 0 | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 8 | 0 | 0 | 0 | 0 | 0 | 0 | 0 | 6 | 0 | 0 | 0 | 0 | 0 |
| 40 | 0 | 0 | 8 | 0 | 0 | 0 | 0 | 0 | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 6 | 0 | 0 | 0 | 0 | 0 | 0 | 0 | 6 | 0 | 0 | 0 | 0 | 0 |
| 41 | 0 | 0 | 8 | 0 | 0 | 0 | 0 | 0 | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 7 | 0 | 0 | 0 | 0 | 0 | 0 | 0 | 5 | 0 | 0 | 0 | 0 | 0 |
| 42 | 0 | 0 | 8 | 0 | 0 | 0 | 0 | 0 | 5 | 0 | 0 | 8 | 0 | 2 | 2 | 3 | 0 | 0 | 0 | 8 | 0 | 0 | 0 | 0 | 0 |
| | | | | | | | | | 1 | 0 | 0 | 8 | 0 | 1 | 0 | 1 | 0 | 0 | 0 | 7 | 0 | 0 | 0 | 0 | 0 |
| 43 | 0 | 0 | 8 | 0 | 0 | 0 | 0 | 0 | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 8 | 0 | 0 | 0 | 0 | 0 | 0 | 0 | 7 | 0 | 0 | 0 | 0 | 0 |
| 44 | 0 | 0 | 6 | 0 | 0 | 0 | 0 | 0 | 5 | 0 | 0 | 8 | 0 | 0 | 0 | 0 | 0 | 0 | 0 | 3 | 0 | 0 | 0 | 0 | 0 |
| | | | | | | | | | 1 | 0 | 0 | 6 | 0 | 0 | 0 | 0 | 0 | 0 | 0 | 0 | 0 | 0 | 0 | 0 | 0 |
| 45 | 0 | 0 | 8 | 0 | 0 | 0 | 0 | 0 | 5 | 0 | 0 | 9 | 0 | 0 | 0 | 0 | 0 | 0 | 0 | 8 | 0 | 0 | 0 | 0 | 0 |
| | | | | | | | | | 1 | 0 | 0 | 8 | 0 | 0 | 0 | 0 | 0 | 0 | 0 | 8 | 0 | 0 | 0 | 0 | 0 |
| 46 | 0 | 0 | 8 | 0 | 0 | 0 | 0 | 0 | 5 | 0 | 0 | 9 | 0 | 0 | 0 | 0 | 0 | 0 | 0 | 8 | 0 | 0 | 0 | 0 | 0 |
| | | | | | | | | | 1 | 0 | 0 | 8 | 0 | 0 | 0 | 0 | 0 | 0 | 0 | 8 | 0 | 0 | 0 | 0 | 0 |

TABLE 2-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 47 | 0 | 0 | 8 | 0 | 0 | 0 | 0 | 0 | 5 | 0 | 0 | 9 | 0 | 0 | 0 | 0 | 0 | 0 | 0 | 8 | 0 | 0 | 0 | 0 | 0 |
| | | | | | | | | | 1 | 0 | 0 | 8 | 0 | 0 | 0 | 0 | 0 | 0 | 0 | 8 | 0 | 0 | 0 | 0 | 0 |
| 48 | 0 | 0 | 8 | 0 | 0 | 0 | 0 | 0 | 5 | 0 | 0 | 9 | 0 | 0 | 0 | 0 | 0 | 0 | 0 | 9 | 0 | 0 | 0 | 0 | 0 |
| | | | | | | | | | 1 | 0 | 0 | 8 | 0 | 0 | 0 | 0 | 0 | 0 | 0 | 8 | 0 | 0 | 0 | 0 | 0 |
| 49 | 0 | 0 | 8 | 0 | 0 | 0 | 0 | 0 | 5 | 0 | 0 | 7 | 0 | 0 | 0 | 0 | 0 | 0 | 0 | 4 | 0 | 0 | 0 | 0 | 0 |
| | | | | | | | | | 1 | 0 | 0 | 6 | 0 | 0 | 0 | 0 | 0 | 0 | 0 | 0 | 0 | 0 | 0 | 0 | 0 |
| 50 | * | * | * | * | * | * | * | * | 5 | 0 | 0 | 8 | 0 | 0 | 0 | 0 | 0 | 0 | 0 | 8 | 0 | 0 | 0 | 0 | 0 |
| | | | | | | | | | 1 | 0 | 0 | 8 | 0 | 0 | 0 | 0 | 0 | 0 | 0 | 8 | 0 | 0 | 0 | 0 | 0 |
| 51 | 0 | 0 | 8 | 0 | 0 | 0 | 0 | 0 | 5 | 0 | 0 | 8 | 0 | 2 | 2 | 2 | 0 | 0 | 0 | 8 | 0 | 0 | 0 | 0 | 0 |
| | | | | | | | | | 1 | 0 | 0 | 8 | 0 | 0 | 0 | 2 | 0 | 0 | 0 | 8 | 0 | 0 | 0 | 0 | 0 |
| 52 | 0 | 0 | 8 | 0 | 0 | 0 | 0 | 0 | 5 | 0 | 0 | 8 | 0 | 1 | 5 | 7 | 3 | 0 | 0 | 4 | 0 | 0 | 2 | 0 | 0 |
| | | | | | | | | | 1 | 0 | 0 | 7 | 0 | 0 | 4 | 2 | 3 | 0 | 0 | 2 | 0 | 0 | 1 | 0 | 0 |
| 53 | 0 | 0 | 8 | 0 | 0 | 0 | 0 | 0 | 5 | 0 | 0 | 8 | 0 | 0 | 0 | 0 | 0 | 0 | 0 | 7 | 0 | 0 | 0 | 0 | 0 |
| | | | | | | | | | 1 | 0 | 0 | 8 | 0 | 0 | 0 | 0 | 0 | 0 | 0 | 6 | 0 | 0 | 0 | 0 | 0 |
| 54 | 0 | 0 | 8 | 0 | 0 | 0 | 0 | 0 | 5 | 0 | 0 | 8 | 0 | 0 | 4 | 0 | 1 | 0 | 0 | 7 | 0 | 0 | 0 | 0 | 0 |
| | | | | | | | | | 1 | 0 | 0 | 8 | 0 | 0 | 2 | 0 | 0 | 0 | 0 | 4 | 0 | 0 | 0 | 0 | 0 |
| 55 | 0 | 1 | 8 | 0 | 0 | 0 | 0 | 0 | 5 | 0 | 0 | 8 | 0 | 3 | 3 | 0 | 0 | 0 | 0 | 8 | 0 | 0 | 0 | 0 | 0 |
| | | | | | | | | | 1 | 0 | 0 | 7 | 0 | 0 | 0 | 0 | 0 | 0 | 0 | 8 | 0 | 0 | 0 | 0 | 0 |

EXAMPLE 57

Paddy Rice Screen

Further biological evaluations were carried out with the compounds of Examples 2, 3, 4 and 5, to assess further the effectiveness of the compounds when used to combat weeds in rice. The tests conducted were paddy tests, in which seedling plants were grown under water containing the test compounds. The test plant species were rice (Oryza sativa, c.v Marathon); Barnyard grass, (Echinocloa crus-galli); Rotala indica; and flatsedge, (Cyperus difformis).

One set of rice and barnyard grass plants, (designated RIT and BGT), were transplanted at 15 days, while another set, (designated RIP and BGP), were direct seeded. RIT, BGT, RIP and BGP were grown in 12.5cm paddy pots without drainage holes. Rotala indica (IR), flatsedge (DC) and further barnyard grass (BG), direct seeded, were grown in 5cm minipots and then placed on gravel in one 12.5cm paddy pot so that they were just below the water level.

Application was at 3 different dosage levels, 3.0, 1.0 and 0.3 kg/ha. Two replicate pots were used for each treatment. Untreated seedling plants were used as controls.

Technical materials were dissolved in the minimum quantity of acetone, (diluted with water and then applied evenly in the appropriate quantity) to the water in each paddy pot with a pipette. The water depth was maintained at 10-20 mm.

Phytotoxicity was assessed in comparison with the untreated control visually using a 0-100 scale (0=no effect, 100=dead) for RIT and a 0-9 scale (0=no effect, 9=dead) for the other species The results are set out in Table 3 below. The results for species assessed on a 0-9 scale have been converted to a percentage rating of effectiveness to facilitate comparison with RIT.

TABLE 3

| Ex. | DOSE (Kg/ha) | RIP | RIT | BGP | BGT | IR | DC | BG |
|---|---|---|---|---|---|---|---|---|
| 2 | 3 | 0.0 | 0.0 | 94.4 | 80.6 | 0.0 | 5.6 | 100.0 |
| | 1 | 0.0 | 0.0 | 75.0 | 55.6 | 0.0 | 0.0 | 58.3 |
| | .3 | 2.8 | 0.0 | 55.6 | 33.3 | 0.0 | 0.0 | 22.2 |
| 3 | 3 | 5.6 | 0.0 | 94.4 | 83.3 | 0.0 | 0.0 | 66.7 |
| | 1 | 0.0 | 0.0 | 94.4 | 80.6 | 0.0 | 5.6 | 83.3 |
| | .3 | 11.1 | 0.0 | 86.1 | 80.6 | 0.0 | 0.0 | 66.7 |
| 5 | 3 | 0.0 | 12.5 | 94.4 | 91.7 | 0.0 | 0.0 | 83.3 |
| | 1 | 0.0 | 0.0 | 94.4 | 88.9 | 0.0 | 0.0 | 75.0 |
| | .3 | 0.0 | 0.0 | 91.7 | 83.3 | 0.0 | 0.0 | 72.2 |
| 4 | 3 | 0.0 | 0.0 | 80.6 | 77.8 | 0.0 | 0.0 | 44.4 |
| | 1 | 0.0 | 0.0 | 72.2 | 63.9 | 0.0 | 0.0 | 22.2 |
| | 0.3 | 0.0 | 0.0 | 33.3 | 0.0 | 0.0 | 0.0 | 0.0 |

I claim:

1. Compound of the formula

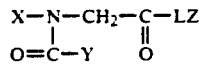

in which

X represents a phenyl group substituted in the 2-position with a cyano group and optionally substituted in one or more of the 3-, 4-, 5-, or 6-positions, the optional substituents in the other positions being halogen, nitro, cyano, amino, mono- or di-($C_{1-4}$ alkyl) amino, $C_{1-4}$ alkyl, $C_{2-4}$ alkenyl, $C_{2-4}$ alkynyl, $C_{1-4}$ haloalkyl and a group of the formula $MR^4$ wherein M represents an oxygen or sulfur atom and $R^4$ represents a hydrogen atom, a $C_{1-8}$ alkyl group, a $C_{1-4}$ haloalkyl group or a phenyl group;

Y represents a phenyl group, optionally substituted with up to 3 moieties selected from the group consisting of halogen, nitro, cyano, amino, mono- or di-($C_{1-4}$ alkyl) amino, $C_{1-4}$ alkyl, $C_{2-4}$ alkenyl, $C_{2-4}$ alkynyl, $C_{1-4}$ haloalkyl, and a group of the formula $MR^4$ wherein M represents an oxygen or sulfur atom and $R^4$ represents a hydrogen atom, a $C_{1-8}$ alkyl group, a $C_{1-4}$ haloalkyl group or a phenyl group;

L represents an oxygen or sulfur atom; and

Z represents a hydrogen atom or a $C_{1-6}$ alkyl group optionally substituted with halogen, cyano, amino, mono- or di($C_{1-4}$ alkyl) amino, $C_{1-4}$ haloalkyl, or a group selected from the formulae $MR^4$ and $(CO)GR^4$ wherein G represents an oxygen or sulfur atom and M and $R^4$ are as defined above, or Z is additionally $C_{3-8}$ cycloalkyl, $C_{2-6}$ alkenyl, $C_{2-6}$ alkynyl, phenyl or phenyl-$C_{1-4}$ alkyl group; and or an amine or alkali metal salt thereof.

2. A compound of the formula I as claimed in claim 1, in which L represents an oxygen atom and Z represents a hydrogen atom or an optionally substituted alkyl group or phenyl or benzyl.

3. A compound as claimed in claim 1 or 2 wherein the group X is optionally substituted by a nitro group or by 1 or 2 halogen atoms.

4. A compound as claimed in claim 3 wherein the group X is substituted in the 3 or 6 position by a halogen atom.

5. A compound as claimed in claim 1 wherein the group Y is optionally substituted by 1 to 3 moieties selected from halogen and nitro, $C_{2-4}$ alkenyl, $C_{1-4}$ alkoxy, $C_{1-4}$ alkylthio, phenoxy, $C_{1-4}$ alkyl and $C_{1-4}$ haloalkyl.

6. A compound as claimed in claim 1, wherein the group Y, when substituted, is substituted at the 4-position.

7. A compound as claimed in claim 1, wherein the group Z represents an alkyl group.

8. A compound as claimed in claim 1, wherein X represents an optionally substituted 2-cyano phenyl group substituted with halogen, alkyl or haloalkyl.

9. A compound as claimed in claim 1, wherein Y represents an optionally substituted phenyl group substituted with halogen, alkyl, alkoxy or cyano.

10. A compound as claimed in claim 1, wherein Z is hydrogen, alkyl, haloalkyl, phenyl-alkyl, or cycloalkyl.

11. A herbicidal composition, comprising a herbicidally effective amount of a compound of formula I, so claimed in claim 1, together with at least one carrier.

12. A method of combating undesired plant growth at a locus by treating the locus with a herbicidally effective amount of a compound of formula I as defined in claim 1, or a composition as claimed in claim 11.

* * * * *